United States Patent [19]

Tegeler et al.

[11] Patent Number: 4,800,200

[45] Date of Patent: Jan. 24, 1989

[54] 4,8-DIHYDRO-8-ARYLISOXAZOLO[4,3-E][1,4]-OXAZEPIN-5(6H)-ONES

[75] Inventors: John J. Tegeler, Bridgewater; Kirk D. Shoger, Piscataway, both of N.J.

[73] Assignee: Hoechst-Roussel Pharmaceuticals Inc., Somerville, N.J.

[21] Appl. No.: 135,763

[22] Filed: Dec. 21, 1987

[51] Int. Cl.[4] .................... A61K 31/55; C07D 498/04
[52] U.S. Cl. .................................. 514/211; 540/490; 548/245
[58] Field of Search ................. 540/490; 514/211

[56] References Cited

U.S. PATENT DOCUMENTS 3,891,630 6/1975 Swett .................................. 540/490
4,590,187 5/1986 Wallach et al. .................... 514/211

FOREIGN PATENT DOCUMENTS 0142361 6/1986 European Pat. Off. ............ 514/211

Primary Examiner—Robert T. Bond
Attorney, Agent, or Firm—Raymond R. Wittekind

[57] ABSTRACT

Novel 4,8-dihydro-8-arylisoxazolo[4,3-e][1,4]oxazepin-5(6H)-ones and methods for treating hypertension utilizing compounds or compositions thereof are disclosed.

17 Claims, No Drawings

4,8-DIHYDRO-8-ARYLISOXAZOLO[4,3-E][1,4]-OXAZEPIN-5(6H)-ONES

This invention relates to compounds of the formula:

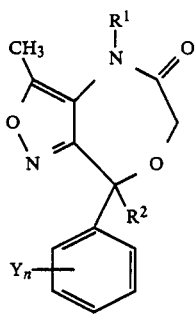

FORMULA I wherein $R^1$ is selected from the group consisting of hydrogen, loweralkyl, arylloweralkyl, aryloxyloweralkyl, cycloalkylloweralkyl, aminoloweralkyl, loweralkylaminoloweralkyl, diloweralkylaminoloweralkyl, and loweralkoxycarbonylloweralkyl; $R^2$ is hydrogen or loweralkyl; Y is independently loweralkyl, loweralkoxy, halogen, trifluoromethyl or nitro; and n is an integer having a value from 0 to 2, inclusive; the geometrical isomers; optical antiopodes, or pharmaceutically acceptable acid addition salts thereof. The 4,8-dihydro-8-arylisoxazolo[4,3-e][1,4]oxazepin-5(6H)-ones of this invention are useful as antihypertensive agents.

Subgeneric to the Formula I compounds of this invention are those compounds where
(a) $R^1$ is hydrogen;
(b) $R^1$ is loweralkyl;
(c) $R^1$ is aralkyl;
(d) $R^1$ is aryloxyloweralkyl;
(e) $R^1$ is cycloalkylloweralkyl;
(f) $R^1$ is aminoloweralkyl;
(g) $R^1$ is loweralkylaminoloweralkyl;
(h) $R^1$ is diloweralkylaminoloweralkyl;
(i) $R^1$ is loweralkoxycarbonylloweralkyl
(j) $R^2$ is hydrogen;
(k) $R^2$ is loweralkyl;
(l) n is zero;
(m) Y is loweralkyl;
(n) Y is loweralkoxy; and
(o) Y is halogen, trifluoromethyl, or nitro.

As used throughout the specification and appended claims, the following definitions shall apply:

"Loweralkyl"—a linear or branched, acyclic hydrocarbon radical containing no unsaturation and having the formula $-C_xH_{2x+1}$ wherein x is an integer having a value of 1 to 7, inclusive, such as methyl, ethyl, 1-propyl, 2-propyl, 1-butyl, 1-pentyl, 3-hexyl, 4-heptyl, and the like.

"Loweralkoxy"—an acyclic organic radical of the formula $-OC_xH_{2x+1}$ wherein x is an integer having a value of 1 to 7, inclusive, such as methoxy, ethoxy, 1- and 2-propoxy, 1,2-dimethylethoxy, 1-butoxy, 1- and 2-pentoxy, 3-hexoxy, 4-heptoxy, and the like.

"Cycloalkyl"—a cyclic hydrocarbon radical of the formula $-C_xH_{2x-1}$ wherein x is an integer having a value of 3 to 7, inclusive, such as cyclopropyl, cyclobutyl, cyclopentyl, cyclohexyl, and cycloheptyl.

"Aryl"—a phenyl group optionally substituted by up to 3 substituents each of which is independently loweralkyl, loweralkoxy, halogen, trifluoromethyl, nitro or cyano.

"Aryloxy"—a monovalent substituent which consists of an aryl group liked through an ether oxygen and having its free valence bond from the ether oxygen.

"Halogen"—a member of the group consisting of fluorine, chlorine, bromine, and iodine radicals.

"Arylloweralkyl"—a loweralkyl group having an aryl substituent thereon.

"Aryloxyloweralkyl"—a loweralkyl group having an aryloxy substituent thereon.

"Cycloalkylloweralkyl"—a loweralkyl group having a cycloalkyl substituent thereon.

"Loweralkoxycarbonyl"—a group of the formula $-C(O)OC_xH_{2x+1}$ wherein x is an integer having a value of 1 to 7 inclusive.

"Loweralkoxycarbonylloweralkyl"—a loweralkyl group having a loweralkoxycarbonyl substituent thereon.

"Amino"—a group of the formula $-NH_2$.
"Loweralkylamino"—a group of the formula

wherein alk is loweralkyl.
"Diloweralkylamino"—a group of the formula

wherein each alk is independently loweralkyl.

"Aminoloweralkyl"—a loweralkyl group having an amino substituent thereon.

"Loweralkylaminoloweralkyl"—a loweralkyl group having a loweralkylamino substituent thereon.

"Diloweralkylaminoloweralkyl"—a loweralkyl group having a diloweralkylamino substituent thereon.

The compounds of this invention are synthesized by the process depicted in the reaction scheme which follows wherein $R^1$, $R^2$, Y and n are as previously defined.

To prepare the parent system, i.e., a 4,8-dihydro-8-arylisoxazolo[4,3-e][1,4]oxazepin-5(6H)-one, 4, a (4-aminoisoxazol-3-yl)phenylmethanone 1 is chloroacetylated to an N-(3-benzoylisoxazol-4-yl)chloroacetamide 2 which is converted to an N-[3-(1-phenyl-1-hydroxyalkyl)-5-methylisoxazol-4-yl]chloroacetamide 3 and then cyclized.

The (4-aminoisoxazol-3-yl)phenylmethanone 1 starting material is known in the art. See, for example, U.S. Pat. No. 4,544,793 describing the preparation of same. Chloroacetylation is accomplished by reacting the (4-aminoisoxazol-3-yl)phenylmethanone 1 with chloroacetyl chloride at a temperature of from about −20° C. to about 40° C., preferably from about 0° C. to about 10° C. in a suitable solvent. Suitable solvents include halogenated hydrocarbons, ethereal solvents and the like such as, for example, dichloromethane, chloroform, diethyl ether, tetrahydrofuran, dimethoxyethane, and the like. Dichloromethane is preferred. The reaction is generally conducted in the presence of a suitable acid scavenger. Suitable acid scavengers include alkali metal carbonates, alkali metal bicarbonates, and tertiary amines (e.g. potassium carbonate, sodium carbonate, potassium bicarbonate, sodium bicarbonate, triethylamine, and the like).

Conversion of the chloroacetamide 2 to the corresponding 1-phenyl-1-hydroxyalkyl derivative 3 is typically accomplished by reaction with an appropriate organolithium or Grignard reagent (i.e. a compound of the formula $R^2Li$ or $R^2MgX$ wherein $R^2$ is loweralkyl and X is halogen, preferably chlorine or bromine. The reaction is ordinarily conducted in a non-reactive organic solvent at a temperature of from about $-70°$ C. to the reflux temperature of the solvent, preferably from about $-35°$ C. to about $0°$ C. Suitable solvents for the reaction include ethereal solvents such as diethyl ether, 1,2-dimethoxyethane, dioxane, tetrahydrofuran, and the like.

Cyclization of the chloroacetamide 3 to the parent system 4 is achieved by reaction with a suitable base (e.g. alkali metal hydrides; sodium hydride being preferred) at a temperature of from about $20°$ C. to the reflux temperature of the solvent medium, reflux temperatures being preferred. Suitable solvents for the cyclization include ethereal solvents as previously described, tetrahydrofuran being preferred.

Substitution of the parent system at the nitrogen atom of the oxazepin ring is achieved by treating the parent system 4 with a suitable base (e.g. alkali metal hydrides, sodium hydride being preferred) and a compound of the formula $R^1X$ wherein $R^1$ is loweralkyl, aralkyl, aryloxyloweralkyl, cycloalkylloweralkyl, aminoloweralkyl, loweralkylaminoloweralkyl, diloweralkylaminoloweralkyl, or loweralkoxycarbonylloweralkyl and X is halogen, preferably iodine, except when $R^1$ is aminoloweralkyl, loweralkylaminoloweralkyl or diloweralkylaminoloweralkyl, then preferably chlorine. The alkylation is generally conducted in a nonreactive organic solvent for example polar aprotic solvents such as for example dimethylformamide, dimethylsulfoxide, hexamethylphosphoramide, and the like (dimethylformamide being preferred), at a temperature of from about $0°$ C. to about $120°$ C., preferably from about $20°$ C. to about $100°$ C.

Compounds of this invention are useful as antihypertensive agents due to their ability to depress blood pressure in mammals. Antihypertensive activity is measured in the spontaneous hypertensive rat by the indirect tail cuff method described by A. Schwartz, Ed., *Methods in Pharmacology*, Vol. I, page 135, Appleton Century Crafts, New York (1971). In this procedure, a group of five animals is treated orally with the drug for three days in relation to a control group of the same number. The drop in blood pressure is measured on the third day following administration. The antihypertensive activity is expressed as mm Hg decrease in systolic blood pressure. A representative compound of this invention along with a standard were tested according to this spontaneous hypertensive rat (SHR) test and were found to produce the results shown in the Table below. The dose is indicated as mg of the compound per kg body weight by oral (PO) administration.

TABLE

| Compound | Dose | SHR, Δ mm Hg |
|---|---|---|
| 4,8-dihydro-3,4,8-trimethyl-8-phenylisoxazol[4,3-e][1,4]-oxazepin-5(6H)—one | 50 mg/kg PO | −99 |
| methyldopa (standard) | 50 mg/kg PO | −40 |

The compounds of this invention are effective in the treatment of hypertension when administered orally, intraperitoneally or intraveneously to a subject requiring such treatment at a dose of from about 0.1 to about 60 mg/kg of body weight per day.

It is to be understood that specific dosage regimens should be adjusted according to the individual need of a particular subject and the professional judgment of the person administering or supervising the administration of the compounds of this invention. Individual requirements will depend on factors which include the age, weight, physical condition, and sex of the subject; as well as the particular administrative method(s) employed.

For the purpose of oral therapeutic administration, the aforesaid compounds may be incorporated with excipients, diluents and/or carriers and used in the form of tablets, troches, capsules, elixirs, suspensions, syrups, wafers, chewing gums and the like. These preparations should contain at least 0.5% of active compound, but may be varied depending upon the particular form and may conveniently be between 4% and 70% of the weight of the unit. The amount of active compound is such that a suitable dosage will be obtained. Preferred compositions and preparations according to the present invention are prepared so that an oral dosage form contains between 1.0 and 300 milligrams of the active compound.

REACTION SCHEME

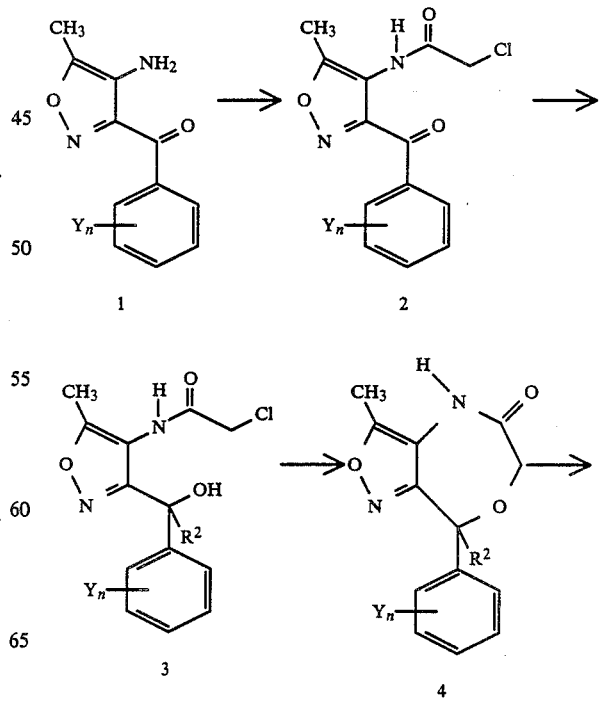

-continued
REACTION SCHEME

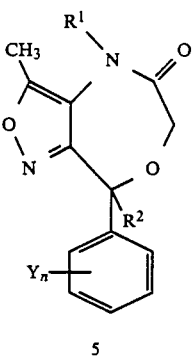

5

The tablets, pills, capsules, troches and the like may also contain the following ingredients: a binder such as microcrystalline cellulose, gum tragacanth or gelatin; an excipient such as starch or lactose, a disintegrating agent such as alginic acid, corn starch and the like; a lubricant such as magnesium stearate; a glidant such as colloidal silicon dioxide; and a sweetening agent such as sucrose or saccharin or a flavoring agent such as peppermint, methyl salicylate, or orange flavoring may be added. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically pure and non-toxic in the amounts used.

For the purposes of parenteral therapeutic administration, the active compounds of the invention may be incorporated into a solution or suspension. These preparations should contain at least 0.1% of active compound, but may be varied between 0.5 and about 50% of the weight thereof. The amount of active compounds in such compositions is such that a suitable dosage will be obtained. Preferred compositions and preparations according to the present invention are prepared so that a parenteral dosage unit contains between 0.5 and 100 milligrams of active compound.

The solutions or suspensions for parenteral administration may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents from the adjustment of tonicity such as sodium chloride or dextrose. The parenteral preparation can be enclosed in ampules or disposable syringes.

Included among the compounds of this invention are:
4,8-dihydro-3-methyl-8-phenylisoxazolo[4,3-e][1,4]oxazepin-5(6H)-one;
4-(2-cyclopropylethyl)-4,8-dihydro-3,8-dimethyl-8-phenylisoxazolo[4,3-e][1,4]oxazepin-5(6H)-one;
4-benzyl-4,8-dihydro-3,8-dimethyl-8-phenylisoxazolo[4,3-e][1,4]oxazepin-5(6H)-one;
4,8-dihydro-8-ethyl-3,4-dimethyl-8-phenylisoxazolo[4,3-e][1,4]oxazepin-5(6H)-one;
4-(4-chlorobenzyl)-4,8-dihydro-3,8-dimethyl-8-phenylisoxazolo[4,3-e][1,4]oxazepin-5(6H)-one;
4,8-dihydro-3,8-dimethyl-4-(3,5-dimethylbenzyl)-8-phenylisoxazolo[4,3-e][1,4]oxazepin-5(6H)-one;
4,8-dihydro-8-(4-methoxyphenyl)-3,4,8-trimethylisoxazolo[4,3-e][1,4]oxazepin-5(6H)-one;
4,8-dihydro-3,4,8-trimethyl-8-(2-methylphenyl)isoxazolo[4,3-e][1,4]oxazepin-5(6H)one;
4-(3-phenylpropyl)-4,8-dihydro-3,8-dimethyl-8-phenylisoxazolo[4,3-e][1,4]oxazepin-5(6H)-one;
4,8-dihydro-3,8-dimethyl-4-(3-dimethylaminopropyl)-8-(3,4-dimethoxyphenyl)isoxazolo[4,3-e][1,4]oxazepin-5(6H)-one;
4,8-dihydro-3,8-dimethyl-8-(3,4-dimethoxyphenyl)isoxazolo[4,3-e][1,4]oxazepin-5(6H)-one;
4,8-dihydro-3,8-dimethyl-4-(2-dimethylaminoethyl)-8-(4-methoxyphenyl)isoxazolo[4,3-e][1,4]oxazepin-5(6H)-one;
4,8-dihydro-3,8-dimethyl-8-(4-methoxyphenyl)isoxazolo[4,3-e][1,4]oxazepin-5(6H)-one;
4,8-dihydro-3,8-dimethyl-8-(4-methylphenyl)isoxazolo[4,3-e][1,4]oxazepin-5(6H)-one;
4,8-dihydro-3,8-dimethyl-8-(3,5-dichlorophenyl)isoxazolo[4,3-e][1,4]oxazepin-5(6H)-one;
4,8-dihydro-3,8-dimethyl-8-(4-trifluoromethylphenyl)isoxazolo[4,3-e][1,4]oxazepin-5(6H)-one; and
4,8-dihydro-3,8-dimethyl-8-(4-nitrophenyl)isoxazolo[4,3-e][1,4]oxazepin-5(6H)-one.

EXAMPLES

The following examples are for illustrative purposes only and are not to be construed as limiting the invention. All temperatures are given in degrees centigrade (°C.). Unless otherwise identified, all percentages are by volume.

EXAMPLE 1

4,8-Dihydro-3,8-dimethyl-8-phenylisoxazolo[4,3-e][1,4]oxazepin-5(6H)-one

Step 1

To a chilled (5° C.) mixture of 6.5 g of (4-amino-5-methylisoxazol-3-yl)phenylmethanone, 65 ml of 2N sodium carbonate, 163 ml of a saturated solution of sodium bicarbonate, and 150 ml of dichloromethane was added, dropwise, 5.1 ml of chloroacetyl chloride. The resulting mixture was stirred for one hour, diluted with dichloromethane and water, and separated. The organic phase was washed with a saturated sodium chloride solution, dried over anhydrous magnesium sulfate and concentrated to an oil. Flash chromatography of the oil (20% ethyl acetate/hexane as the eluent) afforded 7.15 g of N-(3-benzoyl-5-methylisoxazol-4-yl)chloroacetamide, m.p. 86°–88° C.

ANALYSIS: Calculated for $C_{13}H_{11}ClN_2O_3$: 56.02%C, 3.98%H, 10.05%N. Found: 55.87%C, 3.85%H, 9.87%N.

Step 2

To a chilled (−35° C.) solution of 4.53 g of N-(3-benzoyl-5-methylisoxazol-4-yl)chloroacetamide in 33 ml of tetrahydrofuran was added, dropwise under nitrogen, 26.8 ml of methyl lithium as a 1.4M solution in diethyl ether.

The resulting mixture was stirred for 10 minutes at −35° C., quenched with 25 ml of a saturated solution of ammonium chloride and concentrated. The residue was taken up in diethyl ether, washed with a saturated solution of sodium chloride, and dried over anhydrous magnesium sulfate. Concentration afforded a solid which was recrystallized from ethyl acetate/hexane to afford 3.44 g of N-[3-(1-phenyl-1-hydroxyethyl)-5-methylisoxazol-4-yl]chloroacetamide, m.p. 130°-132° C.

ANALYSIS: Calculated for $C_{14}H_{15}N_2O_3Cl$: 57.05%C, 5.13%H, 9.51%N. Found: 57.21%C, 5.07%H, 9.97%N.

Step 3

A solution of 7.25 g of N-[3-(1-phenyl-1-hydroxyethyl)-5-methylisoxazol-4-yl]chloroacetamide in 36 ml of tetrahydrofuran was added, dropwise under nitrogen, to a suspension of sodium hydride, from washing 2.5 g of a 50% (by weight) oil suspension with hexane, in 146 ml of tetrahydrofuran. The resulting mixture was refluxed for two hours, concentrated, and quenched with 250 ml of ice water. The resulting precipitate was collected, washed with hexane and dried under vacuum (phosphorus pentoxide). Recrystallization from methanol afforded 3.25 g of 4,8-dihydro-3,8-dimethyl-8-phenylisoxazolo[4,3-e][1,4]oxazepin-5(6H)-one, m.p. 177°-178° C.

ANALYSIS: Calculated for $C_{14}H_{14}N_2O_3$: 65.10%C, 5.46%H, 10.85%N. Found: 65.06%C, 5.14%H, 10.78%N.

EXAMPLE 2

4,8-Dihydro-3,8-dimethyl-4-(3-phenoxypropyl)-8-phenylisoxazolo[4,3-e][1,4]oxazepin-5(6H)-one Under a nitrogen atmosphere, a suspension of sodium hydride, from washing 707 mg of a 50% (by weight) oil suspension with hexane, in 95 ml of dimethylformamide was combined with 4.0 g of 4,8-dihydro-3,8-dimethyl-8-phenylisoxazolo[4,3-e][1,4]oxazepin-5(6H)-one. To this mixture was added, dropwise, a solution of 4.75 g of 3-phenoxypropyl iodide in 30 ml of dimethylformamide. After stirring for one hour at room temperature, the reaction mixture was quenched with a saturated solution of ammonium chloride and concentrated. The concentrate was taken up in diethyl ether, washed with water (3×100 ml) and a saturated solution of sodium chloride (100 ml), and dried over anhydrous magnesium sulfate. Concentration afforded an oil which was flash chromatographed (3% ethyl acetate/dichloromethane as the eluent) to afford 2.97 g of 4,8-dihydro-3,8-dimethyl-4-(3-phenoxypropyl)-8-phenylisoxazolo[4,3-e][1,4]oxazepin-5(6H)-one, m.p. 118°-120° C.

ANALYSIS: Calculated for $C_{23}H_{24}N_2O_4$: 70.39%C, 6.16%N, 7.14%N. Found: 69.94%C, 6.14%H, 7.19%N.

EXAMPLE 3

4,8-Dihydro-3,4,8-trimethyl-8-phenylisoxazolo[4,3-e][1,4]oxazepin-5(6H)-one

Under a nitrogen atmosphere, a suspension of sodium hydride from washing 1.12 g of a 50% (by weight) oil suspension with hexane, in 150 ml of dimethylformamide was combined with 6.0 g of 4,8-dihydro-3-methyl-8-phenylisoxazolo[4,3-e][1,4]oxazepin-5(6H)-one. To this mixture was added, dropwise, a solution of 1.50 ml of methyl iodide in 75 ml of dimethylformamide. After stirring at room temperature for one hour the reaction mixture was quenched with a saturated solution of ammonium chloride, concentrated and taken up in diethyl ether. The organic phase was washed with water (3×100 ml) and a saturated solution of sodium chloride (100 ml), dried over anhydrous magnesium sulfate, and concentrated to an oil. Flash chromatography (3% ethyl acetate/dichloromethane as the eluent) afforded 4.1 g of 4,8-dihydro-3,4,8-trimethyl-8-phenylisoxazolo[4,3-e][1,4]oxazepin-5(6H)-one, as an oil.

ANALYSIS: Calculated for $C_{15}H_{16}N_2O_3$: 66.16%C, 5.92%H, 10.29%N. Found: 65.73%C, 5.95%H, 10.38%N.

EXAMPLE 4

4,8-Dihydro-3,8-dimethyl-4-(2-dimethylaminoethyl)-8-phenylisoxazolo[4,3-e][1,4]oxazepin-5(6H)-one hydrochloride To a suspension of sodium hydride, from washing 0.74 g of a 50% (by weight) oil suspension with hexane, in 100 ml of dimethylformamide was added 4 g of 4,8-dihydro-3,8-dimethyl-8-phenylisoxazolo[4,3-e][1,4]oxazepin-5(6H)-one. After stirring at room temperature for 1.5 hours, 1.82 g of dimethylaminoethyl chloride was added dropwise, and the reaction mixture heated to 95° C. for 30 minutes. The reaction mixture was then cooled, quenched with 100 ml of a saturated ammonium chloride solution, and extracted with diethyl ether (3×100 ml). The combined extracts were washed with water (2×500 ml), a saturated sodium chloride solution (500 ml) and then dried over anhydrous magnesium sulfate. Concentration afforded 4,8-dihydro-3,8-dimethyl-4-(2-dimethylaminoethyl)-8-phenylisoxazolo-[4,3-e][1,4]oxazepin-5(6H)-one as an oil. The oil was taken up in diethyl ether and treated with ethereal hydrogen chloride to precipitate the corresponding hydrochloride salt. Recrystallization from methanol/diethyl ether afforded 2.79 g of 4,8-dihydro-3,8-dimethyl-4-(2-dimethylaminoethyl)-8-phenylisoxazolo[4,3-e][1,4]oxazepin-5(6H)-one, m.p. 227°-229° C.

ANALYSIS: Calculated for $C_{18}H_{23}N_3O_3 \cdot HCl$: 59.09%C, 6.61%H, 11.49%N. Found: 58.83%C, 6.72%H, 11.40%N.

What is claimed is:

1. A compound of the formula:

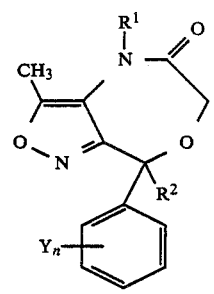

wherein $R^1$ is selected from the group consisting of hydrogen, loweralkyl, arylloweralkyl, aryloxyloweralkyl, cycloalkylloweralkyl, aminoloweralkyl, loweralkylaminoloweralkyl, diloweralkylamnioloweralkyl, and loweralkoxycarbonylloweralkyl; $R^2$ is hydrogen or loweralkyl; Y is independently loweralkyl, loweralkoxy, halogen, trifluoromethyl or nitro; and n is an integer having a value from 0 to 2 inclusive wherein aryl of both arylloweralkyl and aryloxyloweralkyl is phenyl substituted by up to 3 substituents each of which is independently loweralkyl, loweralkoxy, halogen, trifluoromethyl, nitro or cyano and cycloalkyl has 3 to 7 carbon atoms; the geometrical isomers; optical antipodes; or pharmaceutically acceptable acid addition salts thereof.

2. A compound as defined in claim 1 wherein $R^2$ is hydrogen.

3. A compound as defined in claim 2 wherein $R^2$ is loweralkyl.

4. The compound of claim 3 which is 4,8-dihydro-3,8-dimethyl-8-phenylisoxazolo[4,3-e][1,4]oxazepin-5(6H)-one.

5. The compound of claim 3 which is 4,8-dihydro-3,8-dimethyl-4-(3-phenoxypropyl)-8-phenylisoxazolo[4,3-e][1,4]oxazepin-5(6H)-one.

6. The compound of claim 3 which is 4,8-dihydro-3,4,8-trimethyl-8-phenylisoxazolo[4,3-e][1,4]oxazepine-5(6H)-one.

7. The compound of claim 3 which is 4,8-dihydro-3,8-dimethyl-4-(2-dimethylaminoethyl)-8-phenylisoxazolo[4,3-e][1,4]oxazepin-5(6H)-one.

8. A method of reducing blood pressure in mammals comprising administering to a mammal requiring blood pressure reduction, a blood pressure reducing effective amount of a compound as defined in claim 1.

9. An antihypertensive composition comprising an effective blood pressure lowering amount of a compound as defined in claim 1 and a carrier therefor.

10. A process for producing a compound of the formula:

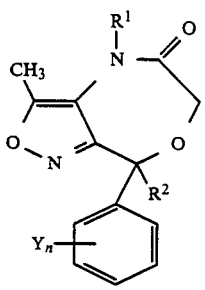

wherein $R^1$ is selected from the group consisting of loweralkyl, arylloweralkyl, aryloxyloweralkyl, cycloalkylloweralkyl, aminoloweralkyl, loweralkylaminoloweralkyl, diloweralkylaminoloweralkyl, and loweralkoxycarbonylloweralkyl; $R^2$ is hydrogen or loweralkyl; Y is independently loweralkyl, loweralkoxy, halogen, trifluoromethyl or nitro; and n is an integer having a value from 0 to 2 wherein aryl of both arylloweralkyl and aryloxyloweralkyl is phenyl substituted by up to 3 substituents each of which is independently loweralkyl, loweralkoxy, halogen, trifluoromethyl, nitro or cyano and cycloalkyl has 3 to 7 carbon atoms; inclusive, which comprises the steps of (a) cyclizing a chloroacetamide of the formula:

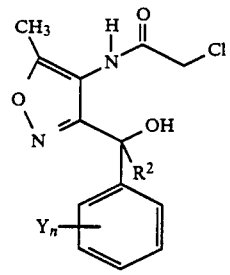

wherein $R^2$, Y and n are as previously described, to a 4,8-dihydro-8-arylisoxazolo[4,3-e][1,4]oxazepin-5(6H)-one of the formula:

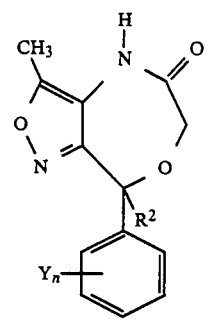

wherein $R^2$, Y and n are as previously described; and (b) reacting the 4,8-dihydro-8-arylisoxazolo[4,3-e][1,4]oxazepin-5(6H)-one with a halide of the formula $R^1X$ where $R^1$ is as previously described and X is halogen.

11. A process as described in claim 10 wherein $R^1$ is loweralkyl, arylloweralkyl, aryloxyloweralkyl, cycloalkylloweralkyl, or loweralkoxycarbonylloweralkyl and X is iodine wherein aryl of both arylloweralkyl and aryloxyloweralkyl is phenyl substituted by up to 3 substituents each of which is independently loweralkyl, loweralkoxy, halogen, trifluoromethyl, nitro or cyano and cycloalkyl has 3 to 7 carbon atoms.

12. A process as described in claim 10 wherein $R^1$ is aminoloweralkyl, loweralkylamino or diloweralkylamino and X is chlorine.

13. A process as described in claim 10 wherein the chloroacetamide is cyclized to the 4,8-dihydro-8-arylisoxazolo[4,3-e][1,4]oxazepin-5(6H)-one by reaction with a base.

14. A process as described in claim 13 wherein the base is an alkali metal hydride.

15. A process as described in claim 14 wherein the cyclization is conducted in the presence of an ethereal solvent at a temperature of from about 20° C. to reflux.

16. A process as described in claim 10 wherein the 4,8-dihydro-8-arylisoxazolo[4,3-e][1,4]oxazepin-5(6H)-one is reacted with the halide $R^1X$ in a nonreactive organic solvent at a temperature of from about 0° C. to about 120° C.

17. A process as described in claim 16 wherein the nonreactive organic solvent is selected from the group consisting of dimethylformamide, dimethylsulfoxide, and hexamethylphosphoramide.

* * * * *

Disclaimer 4,800,200.—*John J. Tegeler*, Bridgewater; *Kirk D. Shoger*, Piscataway, both of N. J. 4,8-DIHDRO-8-ARYLISOXAZOLO[4,3-E] [1,4]-OXAZEPIN-5-(6H)-ONES. Patent dated Jan. 24, 1989. Disclaimer filed Sept. 15, 1989, by the assignee, Hoechst-Roussel Pharmeceuticals, Inc.

Hereby enters this disclaimer to claims 10 to 17 of said patent.

[ *Official Gazette December 5, 1989* ]